US010769763B2

(12) United States Patent
Bauer et al.

(10) Patent No.: US 10,769,763 B2
(45) Date of Patent: Sep. 8, 2020

(54) METHOD FOR RECONSTRUCTING A RECONSTRUCTION DATA SET OF A VESSEL SEGMENT

(71) Applicant: Siemens Healthcare GmbH, Erlangen (DE)

(72) Inventors: Sebastian Bauer, Erlangen (DE); Günter Lauritsch, Nuremberg (DE); Alexander Preuhs, Erlangen (DE); Thomas Redel, Poxdorf (DE); Martin Berger, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 205 days.

(21) Appl. No.: 15/978,696

(22) Filed: May 14, 2018

(65) Prior Publication Data

US 2018/0330484 A1 Nov. 15, 2018

(30) Foreign Application Priority Data

May 15, 2017 (EP) .................... 17171000

(51) Int. Cl.
G06T 5/50 (2006.01)
A61B 6/00 (2006.01)
G06T 7/55 (2017.01)

(52) U.S. Cl.
CPC ............... *G06T 5/50* (2013.01); *A61B 6/504* (2013.01); *G06T 7/55* (2017.01); *A61B 6/481* (2013.01);
(Continued)

(58) Field of Classification Search
CPC .. G06T 5/50; G06T 7/55; A61B 6/504; A61B 6/481
See application file for complete search history.

(56) References Cited

U.S. PATENT DOCUMENTS

| 7,321,677 B2 * | 1/2008 | Evron | A61B 6/504 |
| | | | 128/922 |
| 2003/0078500 A1 * | 4/2003 | Evron | A61B 6/504 |
| | | | 600/443 |

(Continued)

FOREIGN PATENT DOCUMENTS

| DE | 102016210003 A1 | 12/2017 |
| WO | 0185030 A1 | 11/2001 |

OTHER PUBLICATIONS

Sato, Yoshinobu, et al. "A viewpoint determination system for stenosis diagnosis and quantification in coronary angiographic image acquisition." IEEE Transactions on Medical Imaging 17.1 (1998): 121-137.

(Continued)

*Primary Examiner* — Santiago Garcia
(74) *Attorney, Agent, or Firm* — Lempia Summerfield Katz LLC (57) ABSTRACT

A method and system are provided for at least symbolically reconstructing a reconstruction data set of at least one vessel segment in a vessel tree of a patient. Input data for the reconstruction comprises at least two two-dimensional angiographic projection images taken in different acquisition geometries. At least one first angiographic projection image showing the vessel segment is acquired. An evaluation measure is automatically determined for each first angiographic projection image using three-dimensional preliminary information for the vessel segment. The evaluation measure describes the suitability of the at least one angiographic projection image for reconstructing the reconstruction data set. When a quality criterion evaluating the evaluation measure is not fulfilled, at least one additional acquisition geometry is determined using the three-dimensional preliminary information and/or the evaluation measure. In each additional acquisition geometry, at least one (Continued)

second angiographic projection image is acquired. The reconstruction data set is reconstructed from the at least one second angiographic projection image and/or at least one of the at least one first angiographic projection image fulfilling a suitability criterion evaluating the evaluation measure.

20 Claims, 2 Drawing Sheets

(52) U.S. Cl.
CPC ............... *G06T 2207/10116* (2013.01); *G06T 2207/20221* (2013.01); *G06T 2207/30101* (2013.01); *G06T 2211/404* (2013.01)

(56) References Cited

U.S. PATENT DOCUMENTS

| | | | | |
|---|---|---|---|---|
| 2006/0036167 | A1* | 2/2006 | Shina | A61B 6/481 600/433 |
| 2014/0200867 | A1* | 7/2014 | Lavi | G06T 17/00 703/2 |
| 2015/0335304 | A1* | 11/2015 | Lavi | G06F 19/321 600/407 |
| 2015/0339847 | A1* | 11/2015 | Benishti | A61B 6/466 382/131 |
| 2017/0018116 | A1* | 1/2017 | Sun | G06T 7/0012 |
| 2017/0347985 | A1* | 12/2017 | Redel | A61B 6/461 |
| 2018/0330507 | A1* | 11/2018 | Schormans | G06T 7/20 |
| 2019/0159743 | A1* | 5/2019 | Ma | G06T 7/55 |

OTHER PUBLICATIONS

Syngo Workplace—Angio/Quant, Operator Manual, Siemens AG, Medical Solutions, Angiography & Interventional X-Ray Systems, Siemensstr. 1, 91301 Forchheim, www.siemens.com/healthcare, Apr. 2011, pp. 143-189.

Tonino, Pim AL, et al. "Angiographic versus functional severity of coronary artery stenoses in the FAME study: fractional flow reserve versus angiography in multivessel evaluation." Journal of the American College of Cardiology 55.25 (2010): 2816-2821.

Tonino, Pim AL, et al. "Fractional flow reserve versus angiography for guiding percutaneous coronary intervention." New England Journal of Medicine 360.3 (2009): 213-224.

Tröbs, Monique, et al. "Comparison of fractional flow reserve based on computational fluid dynamics modeling using coronary angiographic vessel morphology versus invasively measured fractional flow reserve." American Journal of Cardiology 117.1 (2016): 29-35.

European Search Report for European Patent Application No. 17171000.7-1906, dated Oct. 2, 2017.

* cited by examiner

METHOD FOR RECONSTRUCTING A RECONSTRUCTION DATA SET OF A VESSEL SEGMENT

CROSS REFERENCE TO RELATED APPLICATIONS

This application claims the benefit of EP 17171000.7, filed on May 15, 2017, which is hereby incorporated by reference in its entirety.

FIELD

Embodiments relate to a method for at least symbolically reconstructing a reconstruction data set of at least one vessel segment in a vessel tree of a patient. Input data for the reconstruction includes at least two two-dimensional angiographic projection images taken in different acquisition geometries.

BACKGROUND

Higher dimensional data sets may be reconstructed from at least two lower dimensional data sets, providing a view from different projection directions. For example, three-dimensional data sets may be reconstructed from two-dimensional projection images. If only sparse information in projection space is available, for example in the case of only a few projection images, objects may be symbolically reconstructed, e.g. not calculating attenuation values for each voxel, but only for example boundaries and/or centerlines of objects. Such reconstruction data sets however, at least provide information on the spatial position and extension of the objects.

Reconstruction from sparse sets of projection images, may be used in diagnostic examinations of blood vessels. Lesions, for example stenosis, may be reconstructed from angiographic projection images. A vessel segment is of interest, that may, for example, be marked/manually segmented in the projection images after a few images are acquired. However, the acquired projection images are often not optimally suited for reconstruction, for example regarding overlapping vessels and/or foreshortening, leading to reconstruction errors and uncertainties in evaluating the data.

An field of application is stenosis in the coronary arteries. To treat arteries constricted by atheromatous plaque, stents are used to restore blood flow. As there are also risks associated with minimally invasive insertion of such stents, only hemodynamically relevant stents are treated. The hemodynamic relevance of a stenosis may be assessed by measuring the fractional flow reserve (FFR). While it is known, for example from an article by Tonino et al., "Fractional Flow Reserve versus Angiography for Guiding Percutaneous Coronary Intervention", New England Journal of Medicine 360(3), pp. 213-224, 2009, to invasively measure the FFR, it has recently been proposed to measure the FFR non-invasively, e.g. virtually.

The non-invasive, virtual measurement of FFR provides a secure, fast and inexpensive alternative to a measurement by pressure wire. See for example the article by Monique Trobs et al., "Comparison of Fractional Flow Reserve Based on Computational Fluid Dynamics Modeling Using Coronary Angiographic Vessel Morphology Versus Invasively Measured Fractional Flow Reserve", The American Journal of Cardiology 117 (1), pp. 29-35, 2016. The symbolical reconstruction data set serves as a three-dimensional model, on which computational fluid dynamics (CFD) is performed. The accuracy of the reconstruction is important since the accuracy directly affects the calculation if the FFR and thus the treatment decision.

Reconstruction accuracy is affected by multiple factors. An accurate segmentation of the vessels in the two-dimensional angiographic projection images is necessary. The geometric correlation of the individual angiography scenes may be well estimated that may be impeded by heart and respiratory movement and inaccurate geometrical calibration of the imaging device. The choice of projection directions plays a decisive role. Here, angiographic projection images including a projection direction perpendicular to the vessel segment and a sufficient angle difference to each other are advantageous.

Known reconstruction techniques are based on retrospectively manually choosing suitable angiographic projection images from a preceding acquisition. The acquisition geometries chosen by the medical staff are often not optimal for reconstruction. For example, overlapping vessels may impede segmentation. Furthermore, prospectively shortened (foreshortened) vessel depiction as well as inadequate sets of projection angles may complicate reconstruction.

A workflow is based on using already acquired angiographic projection images and selecting a subset to reconstruct the data set, for example a three-dimensional model. As an example, it is referred to "IZ3D" reconstruction software. The disadvantage of the systems is that the user has to work with data already acquired in acquisition geometries not optimized for reconstruction or acquire additional angiographic projection images, increasing radiation and contrast agent exposure. Additionally, in the workflow, the sequential angiographic projection scenes are acquired independently from each other. In the process, information may be lost.

It has been proposed in not yet laid open patent application DE 10 2016 210 003.3 to acquire additional angiographic projection images in predetermined angular increments along a circular trajectory defined by a rotation axis. The rotation axis is estimated from a first, single angiographic projection image.

BRIEF SUMMARY

The scope of the present invention is defined solely by the appended claims and is not affected to any degree by the statements within this summary. The present embodiments may obviate one or more of the drawbacks or limitations in the related art.

Embodiments provide a method supplying better input data for a reconstruction and thus a qualitatively improved reconstruction data set.

In an embodiment, a method for at least symbolically reconstructing a reconstruction data set of at least one vessel segment in a vessel tree of a patient is provided. Input data for the reconstruction includes at least two two-dimensional angiographic projection images acquired in different acquisition geometries. The method includes acquiring at least one first angiographic projection image showing the vessel segment and automatically determining an evaluation measure for each first angiographic projection image using a three-dimensional preliminary information on the vessel segment, the evaluation measure describing the suitability of the at least one angiographic projection image for reconstructing the reconstruction data set. If a quality criterion evaluating the evaluation measure is not fulfilled, the method determines at least one additional acquisition geometry using the three-dimensional preliminary information and/or the evaluation measure and acquiring, in each additional acquisition geometry, at least one second angiographic projection image and reconstructs the reconstruction data set from the at least one second angiographic projection image and/or at least one of the at least one first angiographic projection image fulfilling a suitability criterion evaluating the evaluation measure.

Three-dimensional preliminary knowledge is used to evaluate the suitability of angiographic projection images and, in case more data is needed, additional acquisition geometries. The modified workflow includes evaluating the already acquired first angiographic projection images. The evaluation may be only one image or may be a set of projection images, as is also true for the second angiographic projection images, as further explained below. Each first angiographic projection image may not be evaluated on its own. Evaluation measures may be applied to multiple angiographic projection images. Each first angiographic projection image is assigned at least one evaluation measure. The quality criterion checks if enough first angiographic projection images (or at least one group) fulfil the suitability criterion to reconstruct solely from the first angiographic projection images in sufficient quality; if it is not fulfilled, second angiographic projection images are acquired to supplement the first angiographic projection images or to even provide all angiographic projection images used for reconstruction if all first angiographic projection images are not suitable to be used, at least not if a certain data quality of the reconstruction data set is aimed at. The approach results in an optimized selection of first angiographic projection images to use in reconstructing and/or, if applicable, in an optimized planning and acquisition of second angiographic projection images. The user may be guided during the examination and an improved foundation for the three-dimensional reconstruction is supplied.

Compared with a pure retrospective selection of angiographic projection images to use for reconstruction, a guided and automatically planned acquisition of additional second angiographic projection images provides for the information from the first angiographic projection images to be included, as opposed to independent acquisition of scenes.

The quality of the reconstructed vessel segment/vessel tree may be improved and kept at a constant high level over multiple patients and examinations. The automatic planning of additional acquisitions results in a faster examination procedure, for example, while also improving diagnostic quality. The necessary radiation exposure and the amount of contrast agent may be reduced since a minimal number of acquisitions may be achieved.

The three-dimensional preliminary information may, for example, describe at least the three-dimensional course and/or position and orientation of the vessel segment and may be approximate and/or based on assumptions. The preliminary information may also describe additional vessels in the vessel tree, for example, all vessels. The preliminary information may include centerlines of the vessel segment and/or further segments/vessels in the vessel tree.

Each angiographic projection image may be derived from or be part of a scene that includes multiple images acquired at different times.

As will be further discussed below, evaluation measures and criteria may be applied or relate to single or multiple angiographic projection images. For example, regarding difference in projection angles, pairs or groups of angiographic projection images/acquisition geometries may be evaluated. Usually, at least the quality criterion will check if at least one group of first angiographic projection images may be found among the first angiographic projection images that allows a reconstruction of a quality aimed at, for example, exceeding a threshold.

It is noted that the method may also be applied to multiple vessel segments, wherein an optimal solution for all the vessel segments is searched. For example, evaluation measures may be calculated for all vessel segments and the quality criterion may consider all the vessel segments. The acquisition geometries may be chosen for the second angiographic projection images such that the minimal number of second angiographic projection images is acquired, reducing radiation exposure for the patient.

Multiple sources of three-dimensional preliminary information exist that may be used. In an embodiment, the three-dimensional preliminary information includes, or is derived from, a previously acquired three-dimensional image data set, for example, a CT data set, that is registered to the imaging device acquiring the angiographic projection images, and/or the three-dimensional preliminary information is determined by preliminary reconstruction from, for example, the at least two first, angiographic projection images, and/or the three-dimensional preliminary information is derived from one two-dimensional first angiographic projection image and at least one assumption on how the acquisition geometry of the first angiographic projection image was chosen.

The three-dimensional preliminary information may include or be derived from a previously acquired three-dimensional image data set of the patient. The image data set may, for example, be a computer tomography data set showing the vessel tree. Using techniques of 2D-3D-registration, for example by registering at least one of the at least one first angiographic projection image to the image data set, the three-dimensional preliminary information may also be used to optimize the reconstruction in a following angiographic examination. Preliminary information may be derived from such an image data set, for example a model of the vessel tree, may be used by registering the underlying image data set or the derived information to the angiographic projection images.

Three-dimensional preliminary information may also be derived from the first angiographic projection images or other available angiographic projection images. A preliminary reconstruction may be performed to derive the three-dimensional preliminary information. The preliminary reconstruction does not need to have a high quality, but mainly serves as a guide for approximate vessel courses. The first angiographic projection images may be used, but it is also possible, to use standard projections acquired from the patient during diagnostics. Alternatively, one or more acquisitions from a heart sweep may also be used for the preliminary reconstruction. The requirements for a sufficiently accurate 3D-reconstruction do not have to be met.

If only one two-dimensional view, for example one two-dimensional first angiographic projection image or scene, is available, it is nonetheless also possible to derive three-dimensional preliminary information. For example, it may be assumed that the vessel segment of interest lies inside or close to the isocenter and/or the projection direction is perpendicular to the course of the vessel segment. Using such assumptions, the three-dimensional orientation of the vessel segment may be estimated, as for example described in DE 10 2016 210 003.3.

The evaluation measure for one first angiographic projection image is determined depending on foreshortening of the vessel segment and/or overlap with other vessels occurring in the acquisition geometry of the evaluated first angiographic projection image. The evaluation measure may describe the quality of the acquisition parameters of an acquisition geometry used for a first angiographic projection image. In a certain angiographic projection image, it may be assessed if the projection direction favors foreshortening and/or vessel overlap. Both effects may be detrimental in reconstruction the more the effects are present. In an embodiment, a foreshortening value is determined by comparing a direction of the vessel segment according to the three-dimensional preliminary information and an image plane according to the acquisition geometry of the first angiographic projection image. The direction of the vessel segment is perpendicular to the projection direction. An overlap measure will be discussed below as the measure is applicable for both evaluation and determination of additional acquisition geometries.

The evaluation measure for a pair of first angiographic projection images may be determined depending on the relative projection angle of the acquisition geometries. The difference in projection angles for a pair of first angiographic projection images is important when assessing the images with respect to reconstruction. The difference in projection angles may be 90° if two angiographic projection images are to be used for reconstruction. The projection directions of the images may be perpendicular.

In an embodiment, to determine the evaluation measure and/or the additional acquisition geometry, an overlap measure for an acquisition geometry is calculated by forward projecting the three-dimensional preliminary information to determine a first virtual projection image relating to the vessel segment of interest and a second virtual projection image relating to other vessels in the vessel tree, deriving a distance weighing image from the first virtual projection image, including a weight decreasing outward from the boundary of the vessel segment in the first virtual projection image, measuring a proximity of other vessels by multiplying the distance weighing image and the second virtual projection image and measuring an overlap by multiplying the first virtual projection image and the second virtual projection image, and deriving the overlap measure by combining the multiplication results.

An overlap measure (overlap metric) may not only be determined automatically, but also includes adjacency in addition to actual overlap. The closer another structure is to the vessel segment of interest, the more likely that segmentation is impeded or error-prone. The determination of an overlap measure may also be used independently from the above-described angiographic workflow. A method for determining at least one acquisition geometry for acquiring angiographic projection images of a vessel segment may be provided where a circular trajectory perpendicular to the vessel segment according to three-dimensional preliminary information is determined and where for different acquisition geometries along the trajectory overlap measures are calculated as described above and acquisition geometries to be used to acquire angiographic projection images are determined based on the overlap measure, for example, such that acquisition geometries having a lower overlap measure are used. An automatic determination of suitable projection directions along the trajectory is provided that may be used for evaluating acquisition geometries of already acquired first angiographic projection images and for determining additional acquisition geometries for second angiographic projection images.

Forward projecting three-dimensional preliminary information to create virtual projection images has already been described, for example by W. Sato et al. in "A viewpoint determination system for stenosis diagnosis and quantification in coronary angiographic image acquisition", IEEE transactions on medical imaging, Vol. 17, No. 1, pages 121 to 137, 1998. However, in the context of foreshortening and vessel overlap, the images have only been displayed to medical staff for further evaluation.

In an embodiment, an automatic determination of an overlap measure is performed, considering actual overlap as well as proximity of other vessels depicted close to the vessel segment of interest. To measure the proximity, a distance weighing image is calculated from the first virtual projection image, such that the boundaries of the vessel segment in the first virtual projection image are determined and a weight is assigned to each pixel outwards from the boundary, decreasing in value away from the boundary. The depiction of the vessel segment inside the boundary, however, is assigned a weight of zero. Also, areas distanced from the boundary by more than a distance limit may also be assigned a weight of zero as image value. If a so-defined distance weighing image and the second virtual projection image are multiplied pixel by pixel, only structures close to the vessel segment in the first virtual projection image are maintained, for example, weighted stronger if the structures are closer to the boundary.

Multiplying the first and second virtual projection images pixel by pixel results in maintaining only overlapping vessel parts, as the first virtual projection image only shows the vessel segment, the second virtual projection image only shows the background, e.g. the other vessels of the vessel tree.

The two multiplication result images may be combined to derive the overlap measure, for example by adding the multiplication result images up and summing over the pixels of the summary result image. Weighing factors may be assigned to each multiplication result image when adding the factors to the summary result image. Actual overlap and adjacency may be differently weighted, that may, however, also be achieved by choosing the weights in the distance weighing image accordingly. The overlap measure may be normalized, for example by dividing the sum over all pixels of the first virtual projection image.

Independent of the actual format of the three-dimensional preliminary information, the first virtual projection image and the second virtual projection image are determined as binary images, simplifying the determination process as described above. An image value is zero if no vessel is present and one otherwise. The virtual projection images may also be confined to a vicinity of the vessel segment.

An embodiment provides that to determine the evaluation measure and/or the additional acquisition geometry, at least one eccentricity of the vessel segment and/or the visibility of at least one bifurcation in the vessel segment are considered. An eccentrically deformed vessel, for example due to stenosis, may appear to have different diameters when imaged with different acquisition geometries. If the eccentric shape of the vessel segment, however, is at least approximately known, it is possible to assess the helpfulness of information derived in a certain acquisition geometry. If, for example, two angiographic projection images of an approximately elliptical vessel segment are each taken at 45° between the long axis and the short axis, the same diameter may be measured and the vessel segment may be assumed circular, such that the acquisition geometries may result in less useful information as, for example, acquisition geometries with a projection direction along the long or short axis of the elliptic shape.

Also, of relevance may be bifurcations along the vessel segment that are to be measured accurately. While in some acquisition geometries, due to overlap, the bifurcation may not or not accurately be visible, other acquisition geometries provide a good view on the actual position of the ostium. Thus, the presence of bifurcations may also be considered when evaluating the suitability of angiographic projection images for reconstruction.

As already explained, depending on the evaluation results, for example, the fulfilment of the quality criteria, the acquisition of further angiographic projection images may result in a considerable improvement of quality of the reconstruction. To plan the acquisition geometries, the three-dimensional preliminary information regarding the vessel segment/vessel tree is used to define the number and acquisition geometry of second angiographic projection images. The calculated evaluation measures may be considered and/or also be calculated for candidate acquisition geometries. An optimal number of additional acquisition geometries may be determined.

When determining additional acquisition geometries, the movement range of the imaging device acquiring the angiographic projection images is considered and/or a time-optimized acquisition order of the second angiographic projection images is determined. Mechanical limits of the imaging device may also limit available acquisition geometries, that is considered when defining additional acquisition geometries. Additionally, the order of the planned scenes/acquisitions may be optimized, for example to minimize the accumulated movement distance of the imaging device and/or the time needed to acquire the second angiographic projection images, such that, in summary, the workflow is improved.

When acquiring second angiographic projection images, the image device is automatically or assistedly positioned to realize the additional acquisition geometries. Acquisition parameters describing the additional acquisition geometries may automatically be communicated to the imaging device such that the additional acquisition geometries may be automatically or at least semi-automatically set by moving respective components of the imaging device. If multiple second angiographic projection images are to be acquired or a scan, for example using a rotation axis, is planned, that covers an angular range more or less than with images, only one acquisition process may be necessary. The movement of the components of the imaging device takes place in the time between measurements, such that arbitrary acquisition parameters may be connected using a single path of the acquisition arrangement of the imaging device.

In an embodiment, the angiographic projection images are acquired using ECG-triggering and/or collimation to a region of interest including the vessel segment, derived from the three-dimensional preliminary information. The second angiographical projection images may be acquired in a certain phase of the cardiac cycle, for example, corresponding to the phase of first angiographic projection images to be used in the reconstruction. The radiation dose for the patient may be further reduced since only one or a few frames are acquired for each acquisition geometry. Regarding collimation, the spatial extent of the vessel segment may be known from the three-dimensional preliminary information, such that, for each additional acquisition geometry, acquisition parameters defining the collimation such that the vessel segment is shown in the second angiographic projection images may be defined, further using the preliminary information and reducing the radiation exposure for the patient.

The tree-dimensional reconstruction, e.g. the determination of the reconstruction data set, may also be assisted using the three-dimensional preliminary information, further or even completely automatizing the process. At least one segmentation step during reconstruction of the reconstruction data set may be performed using the three-dimensional preliminary information. The vessel segment may be localized more simply in the newly acquired second, but also the existing first two-dimensional angiographic projection images, for example by forward projecting the three-dimensional preliminary information. An automatic or semi-automatic two-dimensional segmentation of the vessel segment may be facilitated.

At least a part of the angiographic projection images are geometrically calibrated to each other by 2D-3D-registering the images to the three-dimensional preliminary information. Using the registration, an automated geometric calibration between the different views may be realized, for example as described in US 2017/0018116 A1.

In an embodiment, the method is performed iteratively, using the reconstruction data set as three-dimensional preliminary information. The already improved reconstruction of a first iteration of the method may be used as preliminary information for a further iteration, allowing a further improvement of reconstruction, including the evaluation of the quality of the previous model.

The method may be applied to many examination procedures, for example to determine a model for fluid dynamics simulations. For example, the calculation of decision values, like FFR, may be improved.

Embodiments further provide an angiographic imaging device, including a control device configured to perform the method. All remarks and features pertaining to the method may also be applied respectively to the imaging device, such that the same configurations are provided.

A computer program may be loaded into a storage of a computing device and is configured to perform the steps of a method when the computer program is executed on the computing device. The computing device may be, for example, a control device of an angiographic imaging device. The computer program may be stored on an electronically readable storage medium that includes control information including a computer program, such that when the storage medium is used in a computing device, the steps of the method may be performed by executing the computer program. The electronically readable storage medium according to one or more of the present embodiments may be a non-transient medium, for example a CD-ROM.

DETAILED DESCRIPTION

Figure 1:
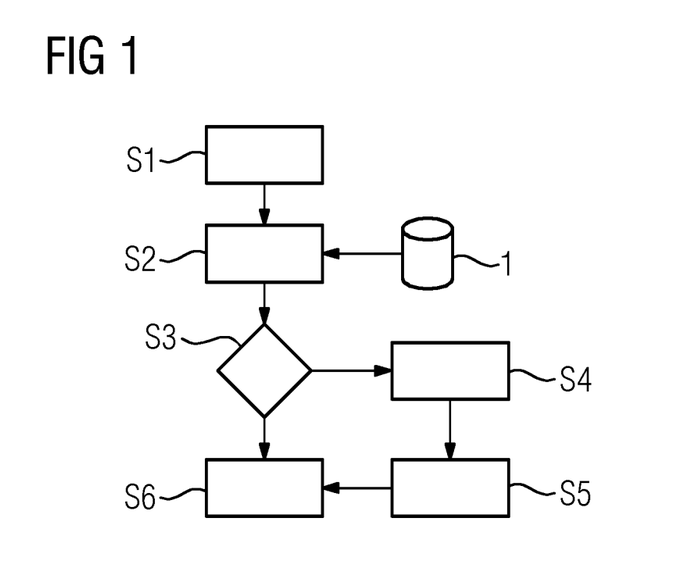
FIG. 1 depicts a flowchart of an embodiment of a method.

FIG. 1 depicts a flowchart of an embodiment of a method. At act S1, at least one first two-dimensional angiographic projection images are acquired using an imaging device, for example an x-ray device including a c-arm and being configured for angiographic use. The acquisition geometry of the at least one first angiographic projection image depicting a vessel segment of interest is determined by a user, for example medical staff. The at least one first angiographic projection image may include a projection direction perpendicular to the course of the vessel segment of interest, that is located isocentric.

The method of FIG. 1 provides a three-dimensional reconstruction data set of the vessel segment, that may, for example, be used as a three-dimensional model for computational fluid dynamics to calculate an FFR value.

At act S2, the first angiographic projection images, e.g. acquisition geometries, are evaluated regarding suitability for the reconstruction process. At least one evaluation measure for each first angiographic projection image and/or pairs or multiple first angiographic projection images may be calculated using three-dimensional preliminary information 1 at least on the vessel segment, for example, providing information on the position and orientation of the vessel segment in three dimensions as well as information on other vessels in the vessel tree of the vessel segment.

According to an embodiment, the three-dimensional preliminary information 1 may be obtained from different sources. The initial preliminary information on the vessel segment needs only be approximate, e.g. a detailed information on the shape of the vessel segment is not necessary, but only the position and orientation of the vessel segment in space.

While the three-dimensional preliminary information 1 may be derived from a proceeding acquisition of the vessel tree of the patient, for example a CT data set or other image data set, that is registered to the imaging device using 2D-3D-registration, the three-dimensional preliminary information may also be based on an initial 3D reconstruction. The initial 3D reconstruction is based on at least two angiographic projection images that are either acquired specifically for the purpose, for example using standard projections or heart sweeps, but may at least include first angiographic projection images to minimize the radiation exposure of the patient. The used angiographic projection images need not fulfil the requirements for a sufficiently accurate three-dimensional reconstruction, since the images are, as discussed above, sufficient to get approximate information on the position and orientation of the vessel segment (and, e.g. for the vessels of the vessel tree) in 3D space.

The three-dimensional preliminary information 1 may also be derived if only one first two-dimensional angiographic projection image or scene is available, by using assumptions, for example, that the projection direction is perpendicular to the course of the vessel segment and that the vessel segment is placed close or in the isocenter of the angiographic imaging device.

Figure 2:
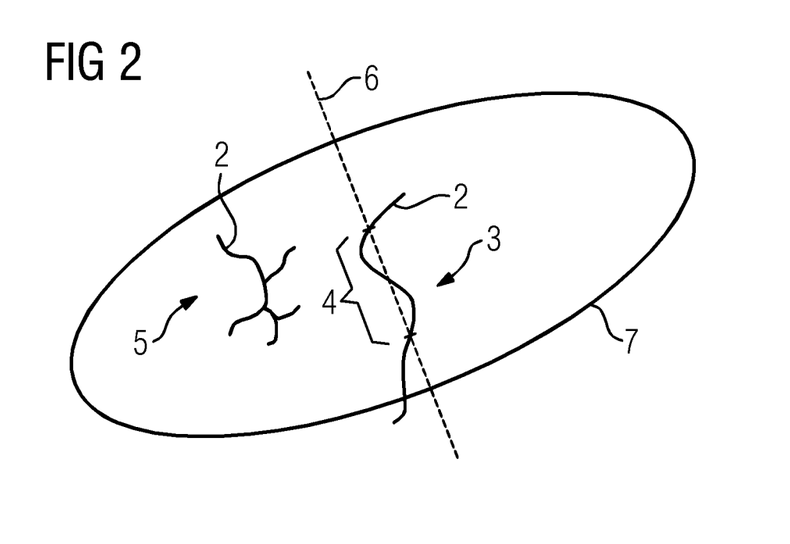
FIG. 2 depicts an example illustration of possible three-dimensional preliminary information.

FIG. 2 depicts an example of such three-dimensional preliminary information 1, including approximate centerlines 2 of the vessel 3 in which the vessel segment 4 is defined and of other vessels 5 in the vessel tree. The course of the vessel segment 4 may be approximately described by a straight line 6. Projection directions are perpendicular to the straight line 6, for example along a circular trajectory 7 using the straight line 6 as rotation axis.

For the evaluation in act S2, multiple factors are considered. The three-dimensional preliminary information 1 as preliminary knowledge may be used to assess the quality and suitability of the first angiographic projection images regarding the three-dimensional reconstruction of the reconstruction data set. The factors considered by one or more evaluation measures are the amount of foreshortening, e.g. the amount of perpendicularity of the projection direction to the straight line 6, the difference in projection angles in a pair or group of first angiographic projection images, a potential eccentricity of the vessel segment and the presence and depiction of bifurcations in the vessel segment. Additionally, the curvature of the vessel segment 4 may be considered further than just defining a straight line 6, for example by minimizing the amount of foreshortening occurring along the length of the vessel segment 4.

Figure 3:
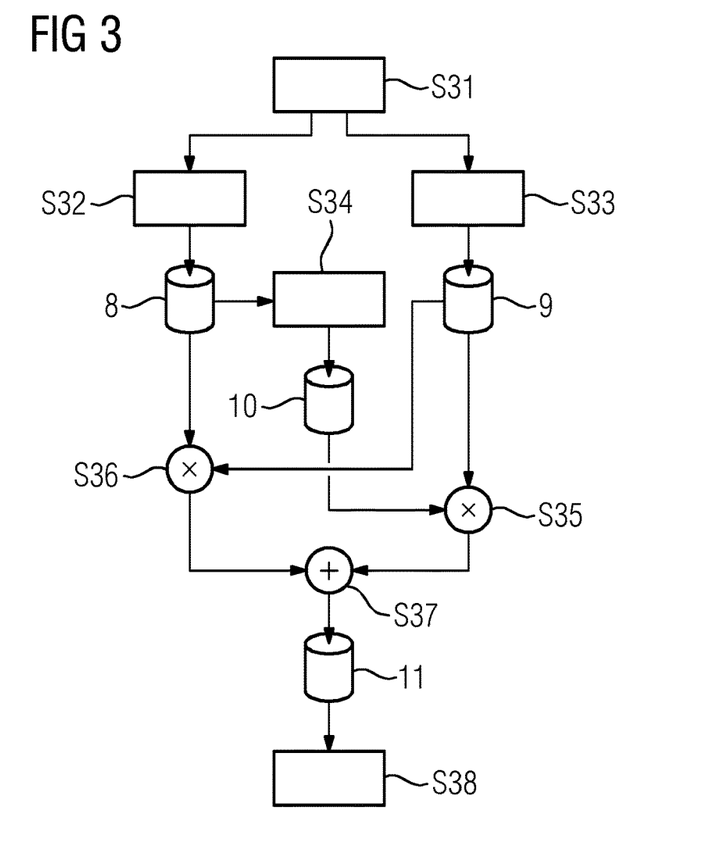
FIG. 3 depicts a flowchart of the determination of an overlap measure according to an embodiment.

Another important factor in evaluating the first angiographic projection images is the overlap of other vessels 5 of the vessel tree onto the depiction of the vessel segment 4. To take the factor into account, an overlap measure is determined for the acquisition geometry of the respective first angiographic projection image. A way of determining an overlap measure (overlap metric) for an acquisition geometry defined relative to the three-dimensional preliminary information 1 is depicted in the flowchart of FIG. 3.

At act S31, if not yet done before, the vessel segment 4 is segmented in the three-dimensional preliminary information 1, for example in a binarized form. The act may be assisted by a user, for example by marking the vessel segment 4 by two clicks along the centerline 2. In the case of the method according to FIG. 1, however, the correspondence may be already known, so that the step S31 has already been performed earlier. The segmentation of the vessel segment 4 allows distinguishing between the vessel segment 4 and other vessels 5 of the vessel tree, that may be termed as "background information" opposed to the "foreground information" of the vessel segment 4. In acts S32 and S33, first and second virtual projection images 8, 9 are determined, by forward projecting the foreground information/background information in the acquisition geometry, respectively.

The virtual projection images 8, 9 may be binary images and may be confined to sub images showing the vessel segment 4 and a vicinity.

At act S34, a distance weighing image 10 is derived from the first virtual projection image 8 by detecting the boundary of the vessel segment 4 in the first virtual projection image 8 and assigning weights decreasing with distance from the boundary to pixels outside the boundary.

Thus, in act S35, by multiplying the distance weighing image 10 and the second virtual projection image 9 pixel by pixel, a first multiplication result image may be obtained describing prominently other vessels 5 depicted in close vicinity to the vessel segment 4.

At act S36, the first virtual projection image 8 and the second virtual projection image 9 are also multiplied pixel by pixel to result in a second multiplication result image depicting actually overlapping vessels 5.

Both multiplication result images may be added in an act S37, where the addition may be performed weighted. The image values of the summary result image 11 may then be added up in a step S38 to determine the overlap measure. The overlap measure is normalized by dividing the sum of the pixel values of summary result image 11 by a sum of the pixel values of first virtual projection image 8.

Such an overlap measure is also calculated for each first angiographic projection image and contributes to the evaluation measure.

The evaluation measure is evaluated in a suitability criterion, that, when fulfilled, selects respective first angiographic projection images for reconstruction of the reconstruction data set; however, the evaluation measures are also evaluated by a quality criterion deciding whether enough sufficiently suitable first angiographic projection images exist to achieve a certain reconstruction quality. The quality criterion is checked in act S3 (FIG. 1).

If the quality criterion is fulfilled, reconstruction of the reconstruction data set may be started in act S6 using the first angiographic projection images fulfilling the suitability criterion. If, however, the quality criterion is not fulfilled in act S3, additional second angiographic projection images are to be acquired.

At act S4, the three-dimensional preliminary information 1 is used again to determine suitable additional acquisition geometries for the second angiographic projection images. For example, the straight line 6 may be used as axis of rotation or to define an axis of rotation, that in turn defines a circular geometry. Acquisition geometries along the trajectory, for example the trajectory 7 of FIG. 2, may be evaluated using the evaluation measures described above, for example, considering the overlap measure. Additionally, limitations in the movement of components of the angiographic imaging device are considered when selecting the additional acquisition geometries. The order of using the additional acquisition geometries is optimized to result in minimal acquisition times and/or movement distances.

At act S5, the planned additional acquisition geometries are transferred to the angiographic imaging device, if not already determined there, such that the additional acquisition geometries may be realized semi-automatically or automatically. The acquisition of the second angiographic projection images may be performed using ECG-triggering. The acquisition parameters defining the additional acquisition geometry also include parameters describing the collimation onto the vessel segment 4, again derived from the three-dimensional preliminary information 1.

At act S6, reconstruction of the reconstruction data set is performed using suitable first angiographic projection images and/or second angiographic projection images. The reconstruction is also assisted by using the three-dimensional preliminary information 1. The preliminary information 1 is used to localize the vessel segment 4 during segmentation of the vessel segment 4, an automatic geometric calibration is performed by 2D-3D-registering the three-dimensional preliminary information 1 to the angiographic projection images used for reconstruction.

It is noted that the method described here may also be performed iteratively by using the resulting reconstruction data set of a first pass as three-dimensional preliminary information 1 for a second pass of the method.

Figure 4:
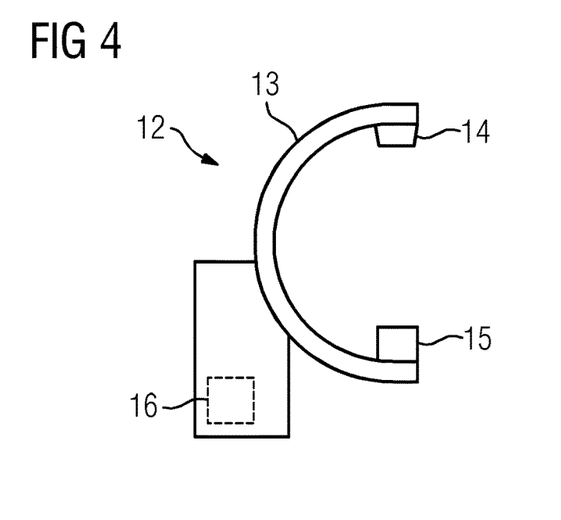
FIG. 4 depicts a principle drawing of an imaging device according to an embodiment.

FIG. 4 depicts a principle drawing of an angiographic imaging device 12. The angiographic imaging device 12 includes a c-arm 13 including an x-ray detector 14 and an x-ray source 15 mounted to opposing ends. The c-arm 13 and/or the components 14, 15 may be moveable to realize certain acquisition geometries.

The x-ray imaging device 12 further includes a control device 16 configured to perform a method. The control device 16 may include an acquisition unit for performing acquisition in determined or chosen acquisition geometries, an evaluation unit for determining evaluation measures, a quality criterion evaluation unit for evaluating the quality criterion, a determination unit for determining additional acquisition geometries and a reconstruction unit for reconstructing the reconstruction data set.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that the dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for at least symbolically reconstructing a reconstruction data set of at least one vessel segment in a vessel tree of a patient, wherein input data for the reconstruction data set comprises at least two two-dimensional angiographic projection images acquired in different acquisition geometries, the method comprising:
acquiring at least one first angiographic projection image depicting the at least one vessel segment;
automatically determining an evaluation measure for the at least one first angiographic projection image using three-dimensional preliminary information for the at least one vessel segment, the evaluation measure describing a suitability of the at least one angiographic projection image for reconstructing the reconstruction data set;
determining, when a quality criterion evaluating the evaluation measure is not fulfilled, at least one additional acquisition geometry using the three-dimensional preliminary information, the evaluation measure, or the three-dimensional preliminary information and the evaluation measure;
acquiring, in each of the at least one determined additional acquisition geometry, at least one second angiographic projection image; and
reconstructing the reconstruction data set from the at least one second angiographic projection image, one or more first angiographic projection images of the at least one first angiographic projection image fulfilling a suitability criterion evaluating the evaluation measure, or a combination thereof.

2. The method of claim 1, wherein the three-dimensional preliminary information comprises or is derived from a previously acquired three-dimensional image data set that is registered to an imaging device acquiring the at least two angiographic projection images, the three-dimensional preliminary information is determined by preliminary reconstruction from the at least one first angiographic projection image, the three-dimensional preliminary information is derived from one of the at least two two-dimensional angiographic projection images and at least one assumption on how the acquisition geometry of the at least one first angiographic projection image was determined, or any combination thereof.

3. The method of claim 2, wherein the previously acquired three-dimensional image data set is a computer tomography (CT) data set.

4. The method of claim 1, wherein the evaluation measure for the at least one first angiographic projection image is determined depending on foreshortening of the at least one vessel segment, overlap with other vessels, or the foreshortening and the overlap occurring in the acquisition geometry of a corresponding first angiographic projection image.

5. The method of claim 4, further comprising determining a foreshortening value, the determining of the foreshortening value comprising comparing a direction of the at least one vessel segment according to the three-dimensional preliminary information and an image plane according to the acquisition geometry of the at least one first angiographic projection image.

6. The method of claim 1, wherein the evaluation measure for a pair of first angiographic projection images is determined depending on a relative projection angle of the acquisition geometries.

7. The method of claim 1, wherein determining the evaluation measure, determining the at least one additional acquisition geometry, or determining the evaluation measure and determining the at least one additional acquisition geometry comprises calculating an overlap measure for an acquisition geometry, the calculating of the overlap measure comprising:
   forward projecting the three-dimensional preliminary information to determine a first virtual projection image relating to the at least one vessel segment and a second virtual projection image relating to other vessels in the vessel tree;
   deriving a distance weighing image from the first virtual projection image, the distance weighting image comprising a weight decreasing outward from a boundary of the at least one vessel segment in the first virtual projection image;
   measuring a proximity of other vessels, the measuring of the proximity of other vessels comprising multiplying the distance weighing image and the second virtual projection image and measuring an overlap by multiplying the first virtual projection image and the second virtual projection image; and
   deriving the overlap measure, the deriving of the overlap measure comprising combining results of the multiplication.

8. The method of claim 1, wherein determining the evaluation measure, determining the at least one additional acquisition geometry, or determining the evaluation measure and determining the at least one additional acquisition geometry include taking at least one eccentricity of the at least one vessel segment, a visibility of at least one bifurcation in the at least one vessel segment, or a combination thereof into account.

9. The method of claim 1, wherein:
   when determining additional acquisition geometries, a movement range of an imaging device acquiring the angiographic projection images is considered, a time-optimized acquisition order of the at least one second angiographic projection image is determined, or a combination thereof;
   when acquiring the at least one second angiographic projection image, the imaging device is automatically or assistedly positioned to realize the additional acquisition geometries; or
   a combination thereof.

10. The method of claim 1, wherein the at least two angiographic projection images are acquired using ECG-triggering, collimation to a region of interest comprising the at least one vessel segment, derived from the three-dimensional preliminary information, or a combination thereof.

11. The method of claim 1, wherein at least one segmentation step during reconstruction of the reconstruction data set is performed using the three-dimensional preliminary information.

12. The method of claim 1, further comprising geometrically calibrating at least a part of the at least one first angiographic projection image and the at least one second angiographic projection image to each other, the geometrically calibrating comprising 2D-3D-registering the at least one first angiographic projection image and the at least one second angiographic projection image to the three-dimensional preliminary information.

13. The method of claim 1, further comprising performing the acquiring of the at least one first angiographic projection image, the automatically determining, the determining, the acquiring of the at least one second angiographic projection image, and the reconstructing iteratively using the reconstruction data set as the three-dimensional preliminary information.

14. An angiographic imaging device for at least symbolically reconstructing a reconstruction data set of at least one vessel segment in a vessel tree of a patient, wherein input data for the reconstruction data set comprises at least two two-dimensional angiographic projection images acquired in different acquisition geometries, the angiographic imaging device comprising:
   an imaging device configured to acquire at least one first angiographic projection image depicting the at least one vessel segment;
   a controller configured to:
      determine an evaluation measure for the at least one first angiographic projection image using three-dimensional preliminary information for the at least one vessel segment, the evaluation measure describing suitability of the at least one first angiographic projection image for reconstructing the reconstruction data set;
      determine, when a quality criterion evaluating the evaluation measure is not fulfilled,
      determine at least one additional acquisition geometry using the three-dimensional preliminary information for determining an additional geometry using the three-dimensional preliminary information, the evaluation measure, or the three-dimensional preliminary information and the evaluation measure; and
      reconstruct the reconstruction data set from the at least one second angiographic projection image and one or more first angiographic projection images of the at least one first angiographic projection image fulfilling a suitability criterion evaluating the evaluation measure.

15. The device of claim 14, wherein the three-dimensional preliminary information comprises or is derived from a previously acquired three-dimensional image data set that is registered to an imaging device acquiring the at least two angiographic projection images, the three-dimensional preliminary information is determined by preliminary reconstruction from the at least one first angiographic projection image, the three-dimensional preliminary information is derived from one of the at least two two-dimensional angiographic projection images and at least one assumption on how the acquisition geometry of the at least one first angiographic projection image was determined, or any combination thereof.

16. The device of claim 15, wherein the previously acquired three-dimensional image data set is a computer tomography (CT) data set.

17. The device of claim 14, wherein determining the evaluation measure, determining the at least one additional acquisition geometry, or determining the evaluation measure and determining the at least one additional acquisition geometry include taking at least one eccentricity of the at least one vessel segment, a visibility of at least one bifurcation in the at least one vessel segment, or a combination thereof into account.

18. A non-transitory computer-readable storage medium storing instructions executable by a controller to reconstruct a reconstruction data set of at least one vessel segment in a vessel tree of a patient, wherein input data for the reconstruction data set comprises at least two two-dimensional angiographic projection images acquired in different acquisition geometries, the instructions comprising:

acquiring at least one first angiographic projection image depicting the at least one vessel segment;

automatically determining an evaluation measure for the at least one first angiographic projection image using three-dimensional preliminary information for the at least one vessel segment, the evaluation measure describing a suitability of the at least one angiographic projection image for reconstructing the reconstruction data set;

determining, when a quality criterion evaluating the evaluation measure is not fulfilled, at least one additional acquisition geometry using the three-dimensional preliminary information, the evaluation measure, or the three-dimensional preliminary information and the evaluation measure;

acquiring, in each of the at least one determined additional acquisition geometry, at least one second angiographic projection image; and reconstructing the reconstruction data set from the at least one second angiographic projection image, one or more first angiographic projection images of the at least one first angiographic projection image fulfilling a suitability criterion evaluating the evaluation measure, or a combination thereof.

19. The computer-readable, non-transitory medium of claim 18, wherein the three-dimensional preliminary information comprises or is derived from a previously acquired three-dimensional image data set that is registered to an imaging device acquiring the at least two angiographic projection images, the three-dimensional preliminary information is determined by preliminary reconstruction from the at least one first angiographic projection image, the three-dimensional preliminary information is derived from one of the at least two two-dimensional angiographic projection images and at least one assumption on how the acquisition geometry of the at least one first angiographic projection image was determined, or any combination thereof.

20. The computer-readable, non-transitory medium of claim 19, wherein the previously acquired three-dimensional image data set is a computer tomography (CT) data set.

* * * * *